(12) United States Patent
Frayne et al.

(10) Patent No.: US 6,896,873 B2
(45) Date of Patent: May 24, 2005

(54) MR SIGNAL-EMITTING COATINGS

(75) Inventors: Richard Frayne, Madison, WI (US);
Charles M. Strother, Madison, WI (US); Orhan Unal, Madison, WI (US); Zhihao Yang, Madison, WI (US); Abukar Wehelie, Madison, WI (US); Hyuk Yu, Blue Mounds, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/096,368

(22) Filed: Mar. 12, 2002

(65) Prior Publication Data

US 2002/0176822 A1 Nov. 28, 2002

Related U.S. Application Data

(63) Continuation of application No. 09/105,033, filed on Jun. 25, 1998, now Pat. No. 6,361,759.
(60) Provisional application No. 60/086,817, filed on May 26, 1998.

(51) Int. Cl.$^7$ ............................................. A61B 5/055
(52) U.S. Cl. .................. 424/9.323; 424/1.11; 424/9.1; 424/9.3; 424/9.32; 424/9.322
(58) Field of Search ............................. 424/1.11, 1.65, 424/9.1, 9.32, 9.322, 9.323, 9.4, 9.5, 9.6, 9.7, 9.8, 9.3

(56) References Cited

U.S. PATENT DOCUMENTS

| | | | |
|---|---|---|---|
| 4,855,353 A | | 8/1989 | Kurami et al. |
| 4,986,980 A | | 1/1991 | Jacobsen |
| 5,039,512 A | | 8/1991 | Kraft et al. |
| 5,087,440 A | | 2/1992 | Cacheris et al. |
| 5,098,692 A | | 3/1992 | Gries et al. |
| 5,264,634 A | | 11/1993 | Becker et al. |
| 5,583,206 A | * | 12/1996 | Snow et al. .................. 534/16 |
| 5,627,079 A | * | 5/1997 | Gardella, Jr. et al. ....... 436/525 |
| 5,744,958 A | | 4/1998 | Werne |
| 5,817,292 A | * | 10/1998 | Snow et al. ............. 424/9.323 |
| 5,932,188 A | * | 8/1999 | Snow et al. ............... 424/1.65 |
| 5,980,862 A | | 11/1999 | Meade et al. |
| 6,361,759 B1 | | 3/2002 | Frayne et al. |
| 6,395,299 B1 | | 5/2002 | Babich et al. |
| 2003/0077225 A1 | | 4/2003 | Laurent et al. |

FOREIGN PATENT DOCUMENTS

| | | |
|---|---|---|
| EP | 0331 616 A2 | 9/1989 |
| WO | WO 92 00748 | 1/1992 |
| WO | WO 94/08629 | 4/1994 |
| WO | WO 94 23782 | 10/1994 |
| WO | WO 95 05669 | 2/1995 |
| WO | WO 95/24225 | 9/1995 |
| WO | WO 96/00588 | 1/1996 |
| WO | WO 98/28258 | 7/1998 |
| WO | WO 01 81460 | 11/2001 |
| WO | WO 02 22186 | 3/2002 |

OTHER PUBLICATIONS

Ladd et al., Proc. ISMRM (1997) 1937.
F.R. Korosec, R. Frayne, T.M. Grist, C.A. Mistretta, 36 Magn. Reson. Medicine, (1996) 345–351.
Fried et al., Image Guided Surgery, Laryngoscope, vol. 106, No. 4, (1996) 411–417.
Xiqun Jiang, et al., Novel Magnetic Resonance Signal Enhancing Coating Material, Advanced Materials, CHG Verlagsgesellschaft, Weinheim, DE, vol. 13, No. 7, Apr. 4, 2001 pp. 490–493.
Database Caplus, Chemical Abstracts Service, Columbus, Ohio, US, Kende, Andrew S., et al. "Synthesis of some novel functionalized double Michael acceptors based on bis (vinylsulfony) methane (BVSM)", retrieved from STN, Database accession No. 1996:721056, XPP002281329 abstract & Organic Preparations and Procedures International, 28(6), 683–690, Coden: Oppiak, ISSN: 0030–4948, 1996.

* cited by examiner

Primary Examiner—Dameron L. Jones
(74) Attorney, Agent, or Firm—Michael Best & Friedrich LLP; Teresa J. Welch; Gregory J. Hartwig

(57) ABSTRACT

The present invention provides a coating that emits magnetic resonance signals and a method for coating medical devices therewith. The coating includes a paramagnetic metal ion-containing polymer complex that facilitates diagnostic and therapeutic techniques by readily visualizing medical devices coated with the complex.

20 Claims, 7 Drawing Sheets

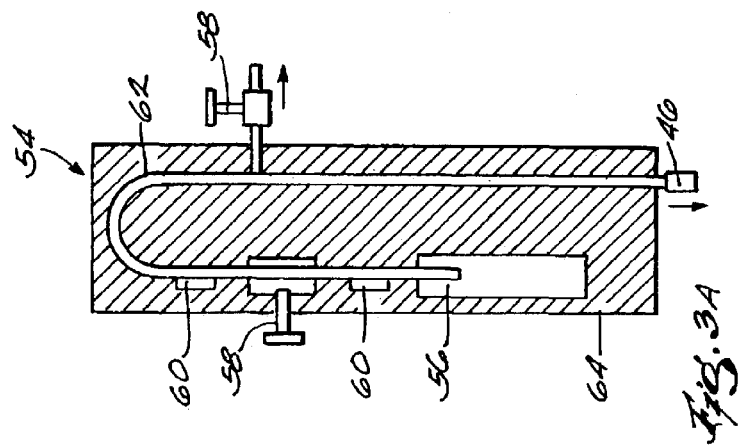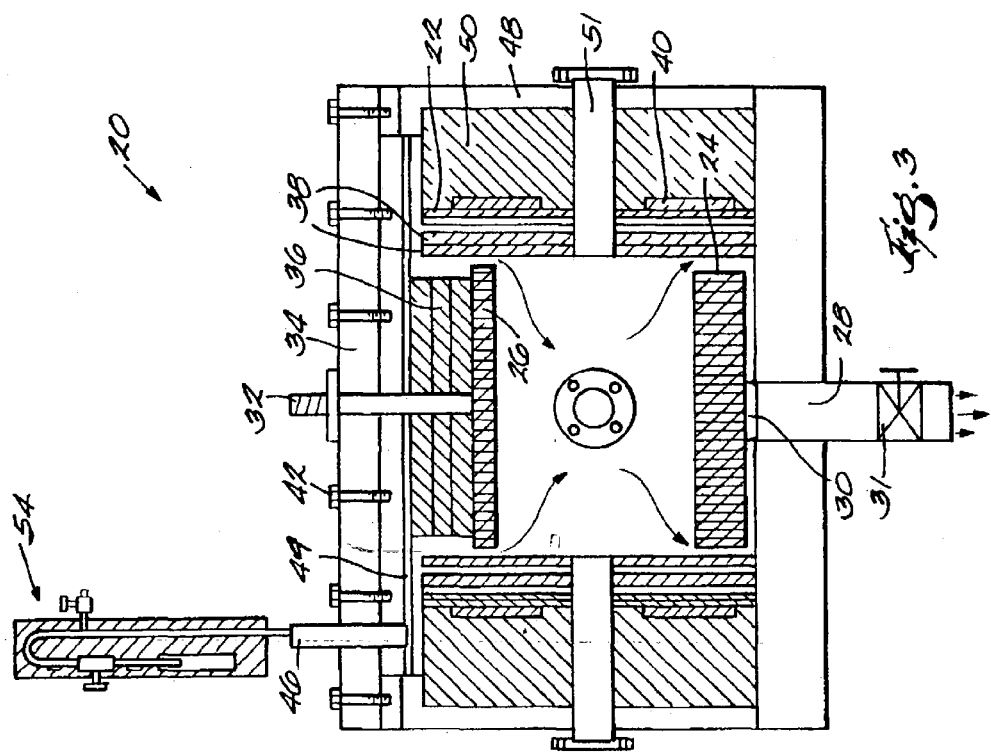

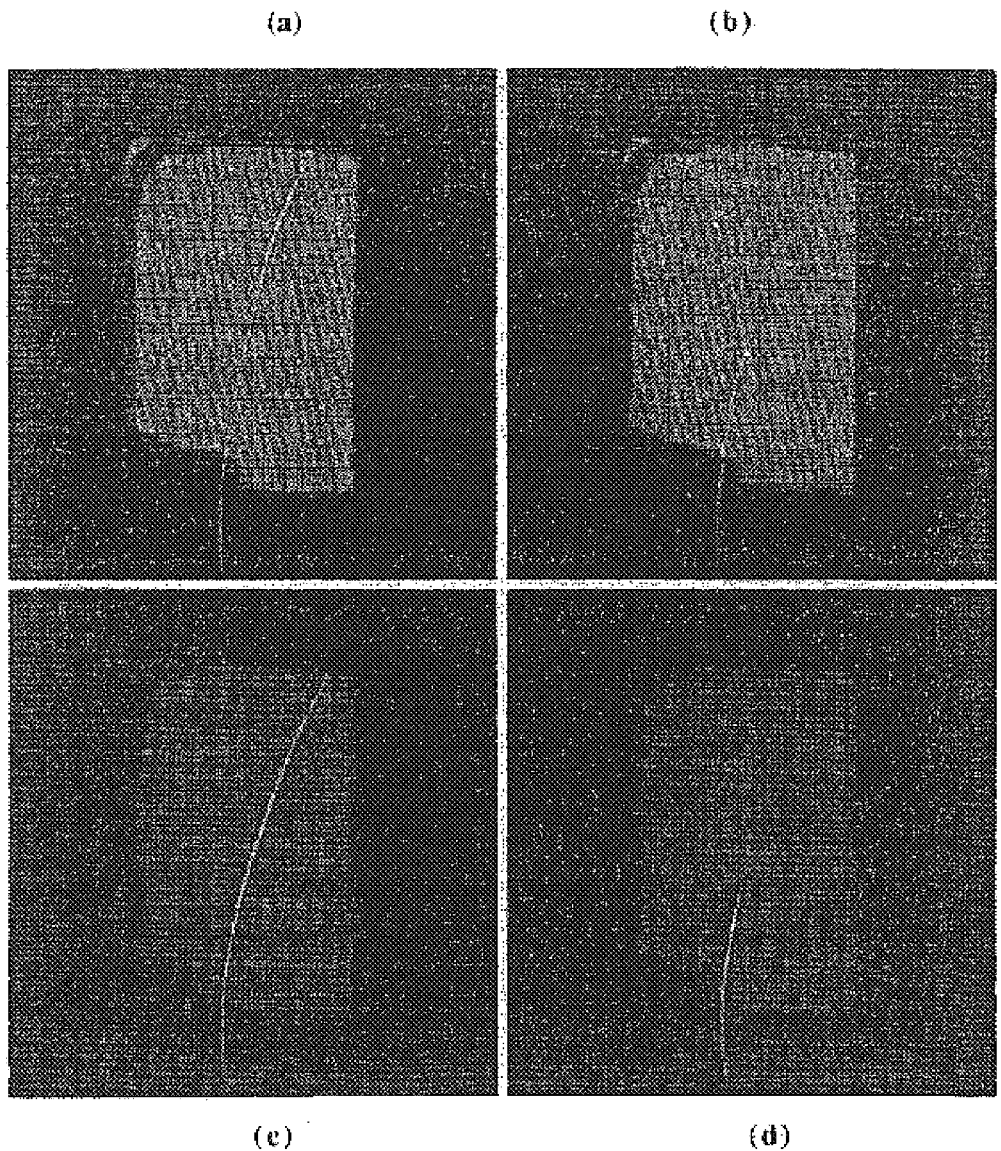

(a,b) Two temporal snapshots from a time series of 27 coronal images of a 6 French catheter filled with Gd-DTPA during movement through a static phantom. Scan parameters: TR = 4.6 msec, TE = 1.3 msec, acquisition matrix = 160 × 256, reconstruction matrix = 256 × 256, FOV = 20 cm × 20 cm, slice thickness = 2 cm, flip angle = 40°, and temporal frame rate = 3 images/sec. Note that the background signal is very high because no projection dephaser was used. (c,d) Similar time frames to those shown in (a) and (b) except that the projection dephaser was enabled. Turning the projection dephaser on gives better background suppression.

FIG. 5

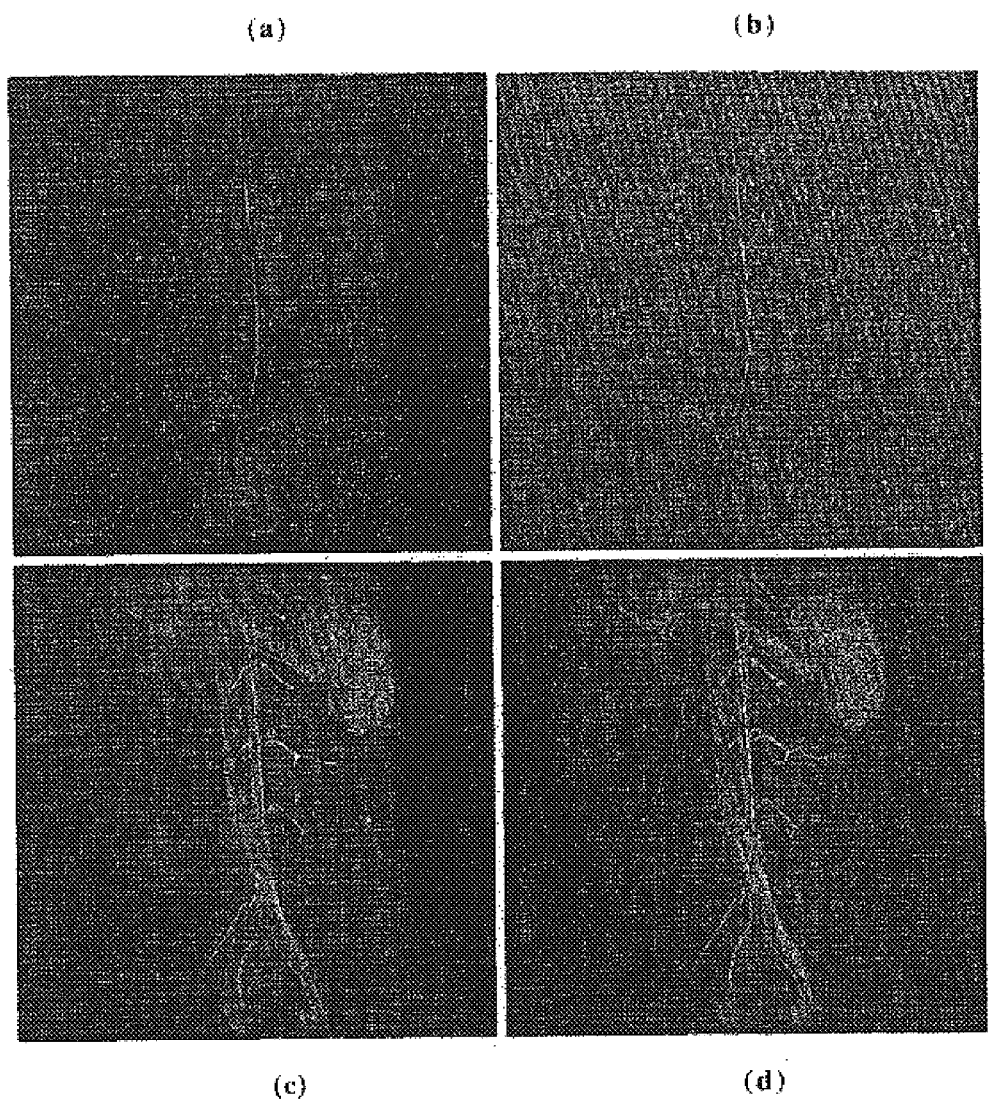

(a) A temporal snapshot of a 6 French catheter filled with Gd-DTPA in the canine aorta with the projection dephaser enabled. (b) The same time frame as in (a) after masking by an image at an earlier time frame. Scan parameters: TR = 4.6 msec, TE = 1.3 msec, acquisition matrix = 160 × 256, reconstruction matrix = 256 × 256, FOV = 20 cm × 20 cm, slice thickness = 2 cm, flip angle = 40°, and temporal frame rate = 3 images/sec. The catheter images in (a) and (b) are shown superimposed onto a previously acquired roadmap image in (c) and (d), respectively, after zero-filling the catheter image by a factor of 2 in both readout and phase encoding directions.

FIG. 7

MR SIGNAL-EMITTING COATINGS

CROSS-REFERENCE TO RELATED APPLICATIONS

This application is a continuation of and claims priority under 35 U.S.C. §120 to U.S. application Ser. No. 09/105,033, which was filed on Jun. 25, 1998 and issued as U.S. Pat. No. 6,361,759 on May 26, 2002, which claims the benefit of the priority date under 35 U.S.C. §119 of U.S. Provisional Application No. 60/086,817 filed on May 26, 1998. Accordingly, this application claims the benefit of the priority date under 35 U.S.C. §119 of U.S. Provisional Application No. 60/086,817 filed on May 26, 1998. The contents of U.S. application Ser. No. 09/105,033, which was filed on June 25, 1998 and issued as U.S. Pat. No. 6,361,759 on May 26, 2002, and U.S. Provisional Application No. 60/086,817 filed on May 26, 1998 are hereby fully incorporated by reference.

STATEMENT REGARDING FEDERALLY SPONSORED RESEARCH OR DEVELOPMENT

This invention was made with Government support under Grant Nos. NIH 1 ROI HL57983; NIH 1 R29 HL57501 awarded by the National Institutes of Health, and NSF-DMR 9711226 and NSF-EEC 8721845(ERC) awarded by the National Science Foundation. The U.S. Government has certain rights in this invention.

BACKGROUND OF THE INVENTION

This invention relates generally to coatings that emit magnetic resonance signals and in particular, to such coatings containing paramagnetic metal ions, and to a process for coating medical devices with such coatings so that the devices are readily visualized in magnetic resonance images during diagnostic or therapeutic procedures done in conjunction with magnetic resonance imaging (MRI).

Since its introduction, magnetic resonance (MR) has been used to a large extent solely for diagnostic applications. With advancement of magnetic resonance imaging, however, it is becoming possible to replace many diagnostic x-ray imaging applications with MR techniques. For example, the accepted standard for staging vascular disease was, at one time, x-ray contrast angiography. Today, MR angiographic techniques are being increasingly used to detect vascular abnormalities and, in some specific clinical instances, contrast-enhanced MR angiograms are rapidly approaching the diagnostic standard set by x-ray angiography.

More recently, advances in MR hardware and imaging sequences have begun to permit the use of MR in certain therapeutic procedures. That is, certain therapeutic procedures or therapies are performed on a patient while the patient and the instruments, devices or agents used and/or implanted are being imaged. The use of MR in this manner of image-guided therapy is often referred to as interventional magnetic resonance (interventional MR). These early applications have included: monitoring ultrasound and laser ablations, guiding the placement of biopsy needles, and visualizing disease, such as tumors, interoperatively.

Of particular interest in interventional MR is endovascular therapy. Endovascular therapy refers to a general class of minimally-invasive interventional (or surgical) techniques which are used to treat vascular abnormalities. Unlike conventional surgical techniques, endovascular therapies access and treat the disease from within the vasculature. The vascular system is usually accessed via the femoral artery. A small incision is made in the groin and the femoral artery punctured. A sheath is then inserted for vascular access. A catheter with the addition of a guide-wire can then be manipulated under fluoroscopic guidance to the area of interest. The guide-wire is then removed from the catheter lumen, and either a therapeutic device (e.g., balloon, stent, coil) is inserted with the appropriate delivery device, or an agent (e.g., embolizing agent, anti-vasospasm agent) is injected through the catheter. In either instance, the catheter functions as a conduit and ensures the accurate and localized delivery of the therapeutic device or agent. Once the device or agent is in place, its delivery system is withdrawn, i.e., the catheter is withdrawn, the sheath removed and the incision closed. The duration of an average endovascular procedure is about 3 hours, although difficult cases may take more than 8 hours. Traditionally, such procedures have been performed under x-ray fluoroscopic guidance.

Performance of these procedures under MR-guidance provides a number of advantages. Safety issues are associated with the relatively large dosages of ionizing radiation required in x-ray fluoroscopy. While radiation risk to the patient is of somewhat less concern (since it is more than offset by the potential benefit of the procedure), exposure to the interventional staff can be a major problem. In addition, the complication rate from MR contrast agents is much less than the commonly used iodinated x-ray contrast agents.

Other advantages of MR-guided procedures include the ability of MR to acquire three-dimensional images. In contrast, most x-ray angiography systems can only acquire a series of projection images. MR has clear advantages when multiple projections or volume reformatting are required in order to understand the treatment of complex three-dimensional vascular abnormalities, such as arterial-venous malformations (AVMs) and aneurysms. Furthermore, MR is sensitive to a variety of "functional" parameters including temperature, blood flow, tissue perfusion, diffusion and brain activation. This additional diagnostic information, which, in principle, may be obtained before, during and immediately after therapy, cannot be acquired by x-ray fluoroscopy alone. It is likely that once suitable MR-based endovascular procedures have been developed, the next challenge will be to integrate this functional information with conventional anatomical imaging and device tracking.

Currently, both "active" and "passive" approaches are being used to monitor the placement of interventional devices under MR guidance. With active tracking, visualization is accomplished by incorporating one or more small radio-frequency (RF) coils into the device, e.g., a catheter. The position of the device is computed from MR signals detected by the coil. Later, this information is superimposed on a previously acquired anatomical "road map" image. The advantages of active tracking include excellent temporal resolution and spatial accuracy, and the ease with which the tip position, e.g., of a catheter, can be updated at 20 Hz, i.e., 20 times per second.

However, active methods allow visualization of only a discrete point(s) on the device. Typically, only the tip of the device is "active", i.e., visualized. Although it is possible to incorporate multiple RF coils (4–6 on typical clinical MR systems) into a device, it is still impossible to determine position at more than a few discrete points along the device. While this may be acceptable for tracking rigid biopsy needles, this is a significant limitation for tracking flexible devices as in endovascular therapy. Furthermore, intravascular heating due to RF-induced currents is a concern with active methods.

As noted above, the attachment of coils onto flexible catheters present numerous challenges. Also, the effect on the mechanical properties of catheters is of concern. Ladd et al. (Ladd et al., Proc. ISMRM (1997) 1937) have addressed some of the deficiencies of an active catheter by designing an RF coil that wraps about the catheter. This allows visualization of a considerable length of a catheter, but still does not address the problems of RF heating and mechanical catheter performance.

Passive tracking technologies use the fact that endovascular devices do not generally emit a detectable MR signal and, thus, result in areas of signal loss or signal voids in MR images. Such signal loss, for example, occurs with a polyethylene catheter. By following the void, the motion of the catheter can be inferred. One advantage of passive tracking methods over active methods is that they do allow "visualization" of the entire length of a device. Signal voids, however, are certainly not optimal for device tracking because they can be confused with other sources of signal loss.

A further source of passive contrast occurs if the device has a magnetic susceptibility much different than tissue (e.g., metallic guide-wires and stents). Susceptibility differences cause local distortions to the magnetic field and result in regions of signal enhancement and of signal loss surrounding the device. A number of published reports describe passive catheter visualization schemes based on signal voids or susceptibility-induced artifacts. A principal drawback of the currently available passive techniques is that visualization is dependent on the orientation of the device with respect to the main magnetic field.

Despite recognition and study of various aspects of the problems of visualization of medical devices in therapeutic, especially endovascular, procedures, the prior art has still not produced satisfactory and reliable techniques for visualization and tracking of the entire device in a procedure under MR guidance.

BRIEF SUMMARY OF THE INVENTION

The present invention provides a process for coating medical devices so that the devices are readily visualized, particularly, in T-1 weighted magnetic resonance images. Because of the high signal caused by the coating, the entirety of the coated devices can be readily visualized during, e.g., an endovascular procedure.

The foregoing, and other advantages of the present invention, are realized thereof in a magnetic resonance (MR) signal-emitting coating which includes a paramagnetic metal ion-containing polymer complex and a method of visualizing medical devices in magnetic resonance imaging, which includes the step of coating the devices with the paramagnetic-ion containing polymer. Specifically, the present invention provides a coating for visualizing medical devices in magnetic resonance imaging, comprising a complex of formula (I):

$$P\text{-}X\text{-}L\text{-}M^{n+} \qquad (I)$$

wherein P is a polymer, X is a surface functional group, L is a chelate, M is a paramagnetic ion and n is an integer that is 2 or greater.

In another aspect, the invention is a coating for visualizing medical devices in magnetic resonance imaging, comprising a complex of formula $$P\text{-}X\text{-}J\text{-}L\text{-}M^{n+} \qquad (II)$$

wherein P is a polymer, X is a surface functional group, L is a chelate, M is a paramagnetic ion, n is an integer that is 2 or greater and J is the linker or spacer molecule.

In a further aspect, the invention is a magnetic resonance imaging system which includes a magnetic resonance device for generating a magnetic resonance image of a target object (as defined hereinafter) in an imaging region (as defined hereinafter) and an instrument for use with the target object in the imaging region. The instrument includes a body sized for use in the target object and a polymeric-paramagnetic ion complex coating in which the complex is represented by formula (I):

$$P\text{-}X\text{-}L\text{-}M^{n+} \qquad (I)$$

wherein P is a polymer, X is a surface functional group, L is a chelate, M is a paramagnetic ion and n is an integer that is 2 or greater.

In yet another aspect, the invention is a method for visualizing medical devices in magnetic resonance imaging which includes the steps of (a) coating the medical device with a polymeric-paramagnetic complex of formula (I):

$$P\text{-}X\text{-}L\text{-}M^{n+} \qquad (I)$$

wherein P is a polymer, X is a surface functional group, L is a chelate, M is a paramagnetic ion and n is an integer that is 2 or greater; (b) positioning the device within a target object; and (c) imaging the target object and coated device.

Other advantages and a fuller appreciation of the specific attributes of this invention will be gained upon an examination of the following drawings, detailed description of preferred embodiments, and appended claims. It is expressly understood that the drawings are for the purpose of illustration and description only, and are not intended as a definition of the limits of the invention.

BRIEF DESCRIPTION OF THE DRAWING(S)

The preferred exemplary embodiment of the present invention will hereinafter be described in conjunction with the appended drawing wherein like designations refer to like elements throughout and in which:

FIGS. 3 and 3A are a schematic representation of a plasma reactor for use in the method of the present invention, FIG. 3A being an enlarged view of the vapor supply assemblage of the plasma reactor of FIG. 3;

FIG. 5 is temporal MR snapshots of a Gd-DTPA-filled catheter;

FIG. 7 is temporal MR snapshots of a Gd-DTPA-filled catheter in a canine aorta.

DETAILED DESCRIPTION OF THE INVENTION

Figure 1:
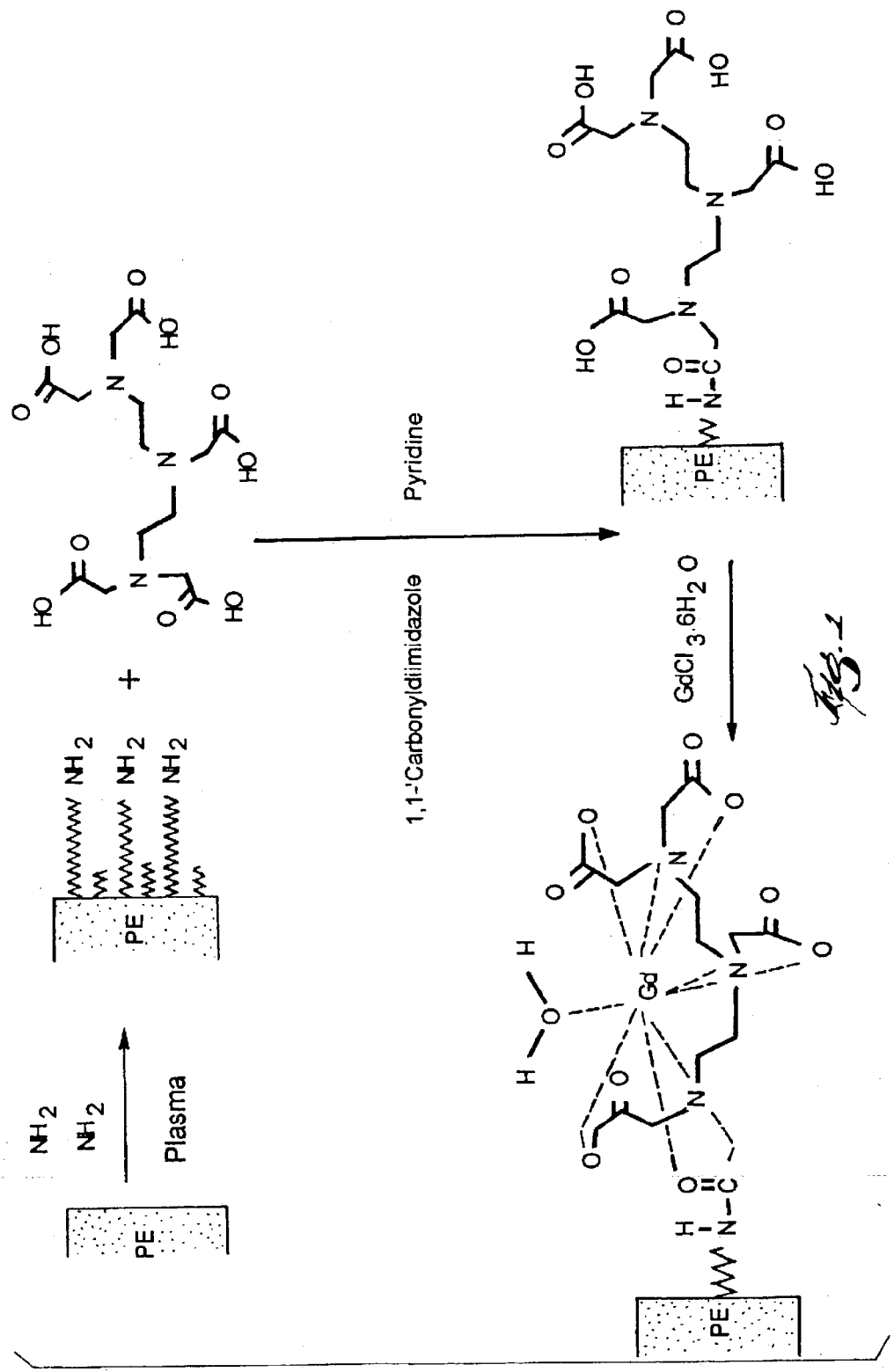
FIG. 1 is a schematic representation of the three-step coating method in accordance with the present invention.

The present invention relates broadly to coating substances that are capable of emitting magnetic resonance signals. The present invention is most particularly adapted for use in coating medical devices so that they are readily visualized in magnetic resonance images. Accordingly, the present invention will now be described in detail with respect to such endeavors; however, those skilled in the art will appreciate that such a description of the invention is meant to be exemplary only and should not be viewed as limitative on the full scope thereof.

The present invention provides coatings containing paramagnetic ions. The coatings of the present invention are characterized by an ability to emit magnetic resonance signals and to permit visualization of the entirety of a device or instrument so coated in interventional MR procedures. The coatings are also of value for providing improved visibility in interoperative MR of surgical instruments after being coated with the signal-enhancing coatings of the present invention. It is also anticipated that the improved visualization of implanted devices so coated, e.g., stents, may find a whole host of applications in diagnostic MR. These attributes of the coating in accordance with the present invention are achieved through a novel combination of physical properties and chemical functionalities.

In the following description of the method of the invention, process steps are carried out at room temperature (RT) and atmospheric pressure unless otherwise specified.

Throughout the specification, the term "medical device" is used in a broad sense to refer to any tool, instrument or other object (e.g., a catheter, biopsy needle, etc.) employed to perform or useful in performing an operation on a target, or a device which itself is implanted in the body (human or animal) for some therapeutic purpose, e.g., a stent, a graft, etc., and a "target" or "target object" being all or part of a human patient or animal positioned in the "imaging region" of a magnetic resonance imaging system (the "imaging region" being the space within an MRI system in which a target can be imaged).

Of particular interest are endovascular procedures performed under MR guidance. Such endovascular procedures include the treatment of partial vascular occlusions with balloons, arterial-venous malformations with embolic agents, aneurysms with stents or coils, as well as subarachnoid hemorrhage (SAH)-induced vasospasm with local applications of papaverine. In these therapeutic procedures, the device or agent is delivered via the lumen of a catheter, the placement of which has traditionally relied on, to varying degrees, x-ray fluoroscopic guidance.

In one aspect, the present invention provides a method of coating the surface of medical devices with a coating which is a polymeric material containing a paramagnetic ion, which coating is generally represented by formula (I):

P-X-L-$M^{n+}$         (I)

wherein P is a polymer, X is a surface functional group such as an amino or a carboxyl group, L is a chelate, M is a paramagnetic ion which binds to L, and n is an integer that is 2 or greater. It is understood that a medical device may be suitably constructed of a polymer whose surface is then functionalized with X, or a medical device may be suitably coated with a polymer whose surface is then suitably functionalized. Such methods for coating are generally known in the art.

To enhance the rotational mobility of $M^{n+}$, the coating optionally contains a linker or spacer molecule J, and is generally represented by the formula (II):

P-X-J-L-$M^{n+}$         (II)

wherein P, X, L and M are as described above and J is the linker or spacer molecule which joins the surface functional group X and the chelate L, i.e., J is an intermediary between the surface functional group and the chelate.

P is suitably any polymer including but not limited to polyethylene, polypropylene, polyesters, polycarbonates, polyamides such as nylon, polytetrafluoroethylene (Teflon™) and polyurethanes that can be surface functionalized with an X group. It is noted that some polymer surfaces may need to be coated further with hydrophilic layers. J is suitably a bifunctional molecule, e.g., a lactam having an available amino group and a carboxyl group, an α,ω-diamine having two available amino groups or a fatty acid anhydride having two available carboxyl groups. X is suitably an amino or carboxyl group. L is suitably any chelate which has a relatively high (e.g., >$10^{20}$) stability constant, K, for the chelate-paramagnetic ion complex. Such chelates include but are not limited to diethylene triamine pentaacetic acid (DTPA), tetraazacyclododecane tetraacetic acid (DOTA) and tetraazacyclo tetradecane tetraacetic acid (TETA). The paramagnetic ion is suitably a multivalent paramagnetic metal including but not limited to the lanthanides and transition metals such as iron, manganese, chromium, cobalt and nickel. Preferably, $M^{n+}$ is a lanthanide which is highly paramagnetic, most preferred of which is the gadolinium(III) ion having seven unpaired electrons in the 4f orbital.

It is noted that the gadolinium(III) (Gd (III)) ion is often used in MR contrast agents, i.e., signal influencing or enhancing agents, because it is highly paramagnetic having a large magnetic moment due to the seven unpaired 4f orbital electrons. In such contrast agents, gadolinium is generally combined with a chelating agent, such as DTPA. The resulting complex (Gd-DTPA or Magnevist; Berlex Imaging, Wayne, N.J.) is very stable in vivo, and has a formation constant of >$10^{23}$, making it safe for human use. Similar agents have been developed by chelating the gadolinium ion with other complexes, e.g., MS-325, Epix Medical, Cambridge, Mass. The gadolinium (III) causes a localized T-1 reduction in the protons in its environment, giving enhanced visibility in T-1 weighed MR images.

The MR signal-emitting coatings in accordance with the present invention are synthesized according to a three or four-step process. The three-step method includes: (i) plasma-treating the surface of a polymeric material (or a material coated with a polymer) to yield surface functional groups, e.g., using a nitrogen-containing gas or vapor such as hydrazine ($NH_2NH_2$) to yield amino groups; (ii) binding a chelating agent, e.g., DTPA, to the surface functional group; and (iii) coordinating a functional paramagnetic metal ion such as Gd(III) with the chelating agent. It is noted that the linkage between the surface functional groups and the chlelates is often an amide-type linkage. In addition to hydrazine, other plasma gases which can be used to provide surface functional amino groups include urea, ammonia, a nitrogen-hydrogen combination or combinations of these gases. Plasma gases which provide surface functional carboxyl groups include carbon dioxide or oxygen.

A schematic reaction process of a preferred embodiment of the present invention is shown in FIG. 1. As seen specifically in FIG. 1, polyethylene is treated with a hydrazine plasma to yield surface functionalized amino groups. The amino groups are reacted with DTPA in the presence of a coupling catalyst, e.g., 1,1'-cabonyldiimidazole, to effect an amide linkage between amino groups and DTPA. The surface amino-DTPA groups are then treated with gadolinium (III) chloride, coordinating the gadolinium (III) ion with the DTPA.

To enhance the rotational component of the interaction of the paramagnetic ion with the environmental water, the MR-signal-emitting coatings are suitably made via a four-step process which is similar to the three-step process except that prior to step (ii), i.e., prior to reaction with the chelating agent, a linker agent or spacer molecule, e.g., a lactam, is bound to the surface functional groups, resulting in the coating of formula (II).

Figure 2:
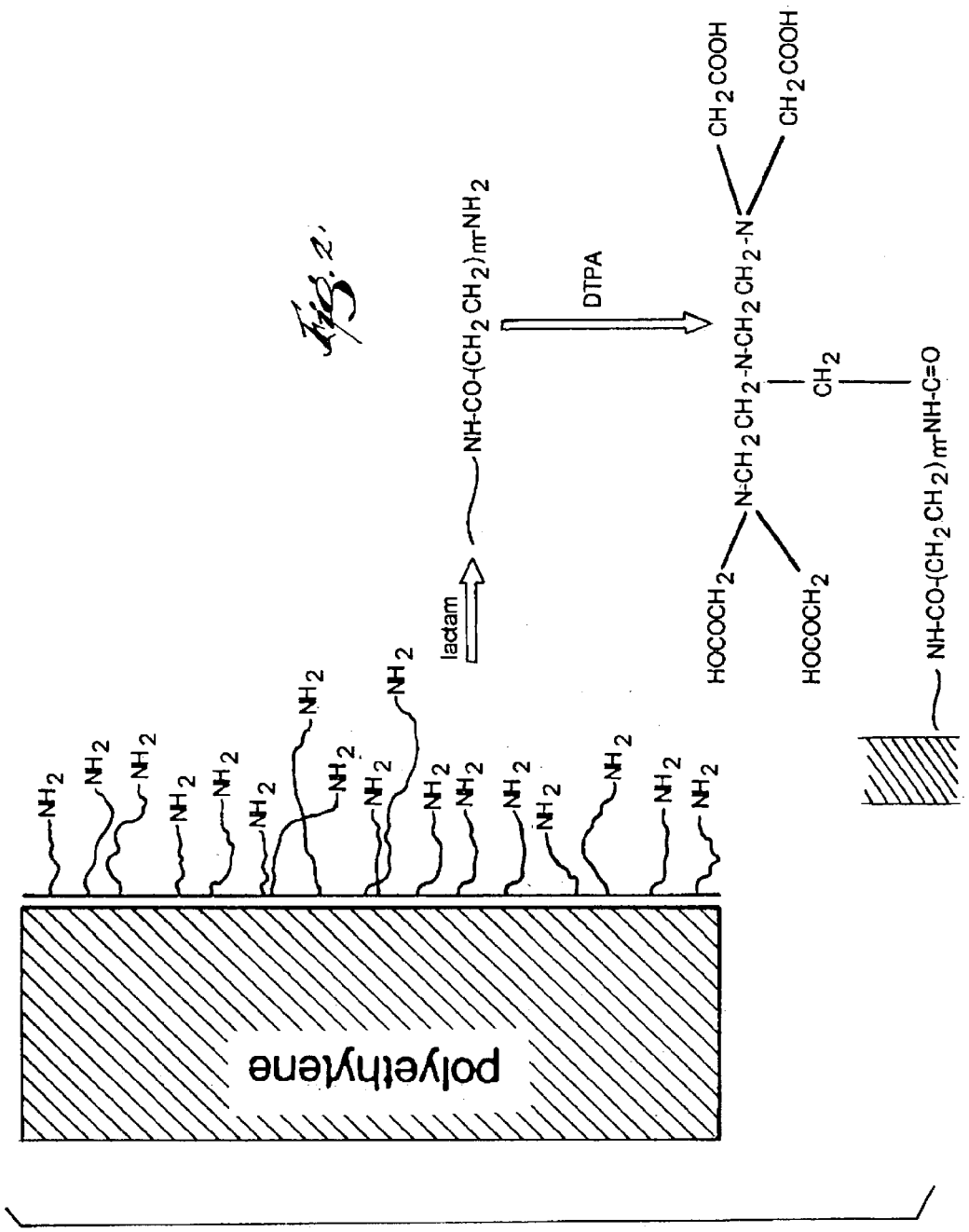
FIG. 2 is a schematic representation of the four-step coating method using a linker agent.

An illustrative schematic reaction process using a lactam is shown in FIG. 2. As seen in FIG. 2, a polyethylene with an amino functionalized surface is reacted with a lactam. The amino groups and lactam molecules are coupled via an amide linkage. It is noted that "m" in the designation of the amino-lactam linkage is suitably an integer greater than 1. The polyethylene-amino-lactam complex is then reacted with DTPA which forms a second amide linkage at the distal end of the lactam molecule. The last step in the process, coordinating the gadolinium (III) ion with the DTPA (not shown in FIG. 2), is the same as shown in FIG. 1.

Specific reaction conditions for forming a coating in accordance with the present invention, which utilizes surface functionalized amino groups, include plasma treatment of a polymeric surface, e.g., a polyethylene surface, at 50 W power input in a hydrazine atmosphere within a plasma chamber, schematically represented in FIG. 3, for 5–6 min. at 13 Pa to 106 Pa (100 mT-800 mT).

As seen in FIG. 3, an exemplary plasma chamber, designated generally by reference numeral 20, includes a cylindrical stainless steel reaction chamber 22 suitably having a 20 cm diameter, a lower electrode 24, which is grounded, and an upper electrode 26, both suitably constructed of stainless steel. Electrodes 24 and 26 are suitably 0.8 cm thick. Upper electrode 26 is connected to an RF-power supply (not shown). Both electrodes are removable which facilitates post-plasma cleaning operations. Lower electrode 24 also forms part of a vacuum line 28 through a supporting conical-shaped and circularly-perforated stainless steel tubing 30 that has a control valve 31. The evacuation of chamber 22 is performed uniformly through a narrow gap (3 mm) existing between lower electrode 24 and the bottom of chamber 22. Upper electrode 26 is directly connected to a threaded end of a vacuum-tight metal/ceramic feedthrough 32 which assures both the insulation of the RF-power line from the reactor and the dissipation of the RF-power to the electrodes. A space 34 between upper electrode 26 and the upper wall of chamber 22 is occupied by three removable 1 cm thick, 20 cm diameter Pyrex™ glass disks 36. Disks 36 insulate upper electrode 26 from the stainless steel top of the reactor 20 and allow the adjustment of the electrode gap. The reactor volume located outside the perimeter of the electrodes is occupied by two Pyrex™ glass cylinders 38 provided with four symmetrically located through-holes 40 for diagnostic purposes.

This reactor configuration substantially eliminates the non-plasma zones of the gas environment and considerably reduces the radial diffusion of the plasma species, consequently leading to more uniform plasma exposure of the substrates (electrodes). As a result, uniform surface treatment and deposition processes (6–10% film thickness variation) can be achieved.

The removable top part of the reactor 20 vacuum seals chamber 22 with the aid of a copper gasket and fastening bolts 42. This part of the reactor also accommodates a narrow circular gas-mixing chamber 44 provided with a shower-type 0.5 mm diameter orifice system, and a gas- and monomer supply connection 46. This gas supply configuration assures a uniform penetration and flow of gases and vapors through the reaction zone. The entire reactor 20 is thermostated by electric heaters attached to the outside surface of chamber 22 and embedded in an aluminum sheet 48 protecting a glass-wool blanket 50 to avoid extensive loss of thermal energy.

For diagnostic purposes, four symmetrically positioned stainless steel port hole tubings 51 are connected and welded through insulating blanket 50 to the reactor wall. These port holes are provided with exchangable, optically smooth, quartz windows 52. A vapor supply assemblage 54, as seen in FIG. 3A, includes a plasma reservoir 56, valves 58, VCR connectors 60 and connecting stainless steel tubing 62. Assemblage 54 is embedded in two 1 cm thick copper jackets 64 provided with controlled electric heaters to process low volatility chemicals. Assemblage 54 is insulated using a glass-wool blanket coating. The thermostatic capabilities of reactor 20 are in the range of 25–250° C.

Once the device to be coated is surface functionalized, it is then immersed in a solution of the chelating agent, e.g., DTPA, in, e.g., anhydrous pyridine, typically with a coupling catalyst, e.g., 1,1'-carbonyidiimidazole, for a time sufficient for the chelate to react with the amine groups, e.g., 20 hours. The surface is washed sequentially with solvents, e.g., pyridine, chloroform, methanol and water. The chelate-treated surface is then soaked in a solution of a salt of the paramagnetic ion, e.g., $GdCl_3.6H_2O$ in water, for a time sufficient for the paramagnetic ion to react with the chelate, e.g., 12 hours. The surface is then washed with water.

In test processes, each step has been verified to confirm that the bonding, in fact, occurs. To verify the amino group functionalization, x-ray photoelectron spectroscopy (XPS) was used. A XPS spectrum of the polyethylene surface was taken prior to and after plasma treatment. The XPS spectrum of polyethylene before the treatment showed no nitrogen peak. After treatment, the nitrogen peak was 5.2% relative to carbon and oxygen peaks of 63.2% and 31.6%, respectively.

To determine whether the amino groups were accessible for chemical reactions, after step (i) the surface was reacted with p-fluorophenone propionic acid and rinsed with solvent (tetrahydrofuran). This reactant, chosen because of good sensitivity of fluorine atoms to XPS, produces many photoelectrons upon x-ray excitation. The result of the XPS experiment showed a significant fluorine signal. The peaks for fluorine, nitrogen, carbon and oxygen were: 3.2%, 1.5%, 75.7% and 19.6%, respectively. This demonstrated that the amino groups were accessible and capable of chemical reaction.

Because the coatings in accordance with the present invention are advantageously applied to catheters and because a catheter surface is cylindrical, it is noted that to coat commercial catheters, the plasma reaction must be carried out by rotating the catheter axis normal to the plasma sheath propagation direction. Such rotational devices are known and can be readily used in the plasma reactor depicted in FIG. 3. To verify that surface amination occurs for such surfaces, atomic force spectroscopy (AFM) is used to study the surface morphology because XPS requires a well-defined planar surface relative to the incident X-ray coated, the coating densities (e.g., nmol $Gd^{3+}/m^2$) are measured using NMR and optimal coating densities can be determined.

It is also understood that metallic surfaces can be treated with the coatings in accordance with the present invention. Metallic surfaces, e.g., guide-wires, can be coated with polymer, e.g., polyethylene, by various known surface-coating techniques, e.g., melt coating, a well known procedure to overcoat polymers on metal surfaces. Once the metallic surfaces are overcoated with polymer, all other chemical steps as described herein apply.

The present invention is further explained by the following examples which should not be construed by way of limiting the scope of the present invention.

EXAMPLE 1

Preparation of Coated Polyethylene Sheets

Polyethylene sheets were coated in the three-step process described herein.

Surface Amination.

A polyethylene sheet (4.5 in diameter and 1 mil thick) was placed in a capacitively coupled, 50 kHz, stainless steel plasma reactor (as shown schematically in FIGS. 3 and 3A) and hydrazine plasma treatment of the polyethylene film was performed. The substrate film was placed on the lower electrode. First, the base pressure was established in the reactor. Then, the hydrazine pressure was slowly raised by opening the valve to the liquid hydrazine reservoir. The following plasma conditions were used: base pressure=60 mT; treatment hydrazine pressure=350 mT; RF Power=25 W; treatment time=5 min; source temperature (hydrazine reservoir)=60° C.; temperature of substrate=40° C. Surface atomic composition of untreated and plasma-treated surfaces were evaluated using XPS (Perkin-Elmer Phi-5400; 300 W power; Mg source; 15 kV; 45° angle).

DTPA Coating.

In a 25 mL dry flask, 21.5 mg of DTPA was added to 8 mL of anhydrous pyridine. In a small vessel, 8.9 mg of carbonyidiimidazole (CDI), as a coupling catalyst, was dissolved in 2 mL of anhydrous pyridine. The CDI solution was slowly added into the reaction flask while stirring, and the mixture was stirred at room temperature for 2 hours. The solution was then poured into a dry Petri dish, and the hydrazine-plasma treated polyethylene film was immersed in the solution. The Petri dish was sealed in a desiccator after being purged with dry argon for 10 min. After reaction for 20 hours, the polyethylene film was carefully washed in sequence with pyridine, chloroform, methanol and water. The surface was checked with XPS, w and the results showed the presence of carboxyl groups, which demonstrate the presence of DTPA.

Gadolinium (III) Coordination.

0.70 g of $GdCl_3 \cdot 6H_2O$ was dissolved in 100 mL of water. The DTPA-treated polyethylene film was soaked in the solution for 12 hr. The film was washed with water. The surface was checked with XPS and showed two peaks at a binding energy (BE)=153.4 eV and BE=148.0 eV, corresponding to chelated $Gd^{3+}$ and free $Gd^{3+}$, respectively. The film was repeatedly washed with water until the free $Gd^{3+}$ peak at 148.0 eV disappeared from the XPS spectrum.

The results of the treatment in terms of relative surface atomic concentration are given below in Table 1.

TABLE 1

Relative Surface Atomic concentration of untreated and treated PE surfaces

|  | % Gd | % N | % O | % C |
|---|---|---|---|---|
| Untreated PE | 0.0 | 0.0 | 2.6 | 97.4 |
| Hydrazine plasma treated PE | 0.0 | 15.3 | 14.5 | 70.2 |
| DTPA coated PE | 0.0 | 5.0 | 37.8 | 57.2 |
| Gd coated PE | 1.1 | 3.7 | 35.0 | 60.3 |

EXAMPLE 2

Preparation of Coated Polyethylene Sheets Including Linker Agent

Coated polyethylene sheets are prepared according to the method of Example 1, except that after surface amination, the polyethylene sheet is reacted with a lactam, and the sheet washed before proceeding to the chelation step. The surface of the film is checked for amine groups using XPS.

EXAMPLE 3

Imaging of Coated Polyethylene and Polypropylene Sheets

Figure 4:
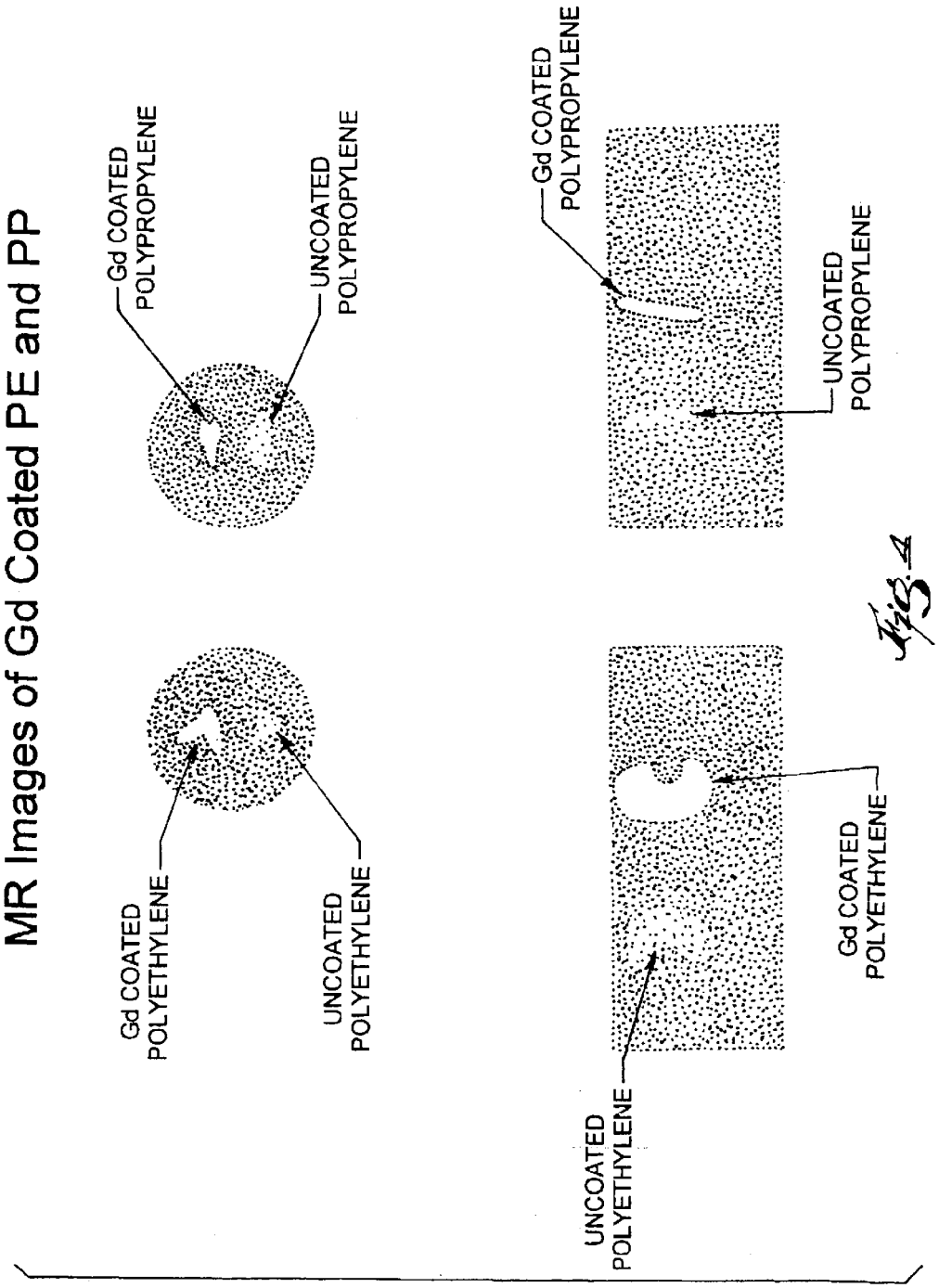
FIG. 4 is several MR images of coated devices in accordance with the present invention.

MR signal enhancement was assessed by imaging coated sheets of polyethylene and polypropylene, prepared as described in Example 1, with gradient-recalled echo (GRE) and spin-echo (SE) techniques on a clinical 1.5 T scanner. The sheets were held stationary in a beaker filled with a tissue-mimic, yogurt, and the contrast-enhancement of the coating was calculated by normalizing the signal near the sheet by the yogurt signal. The T1-weighed GRE and SE MR images showed signal enhancement near the coated polymer sheet. The T1 estimates near the coated surface and in the yogurt were 0.4 s and 1.1 s, respectively. No enhancement was observed near control sheets. The MR images acquired are shown in FIG. 4.

EXAMPLE 4

In vitro Testing of Gd-DTPA Filled Catheter Visualization

The following examples demonstrated the utility of Gd-DTPA in visualizing a catheter under MR guidance.

A Gd-DTPA-filled single lumen catheter 3–6 French (1–2 mm) was imaged in an acrylic phantom using a conventional MR Scanner (1.5T Signa, General Electric Medical Systems) while it was moved manually by discrete intervals over a predetermined distance in either the readout direction or the phase encoding direction. The phantom consisted of a block of acrylic into which a series of channels had been drilled. The setup permitted determination of the tip position of the catheter with an accuracy of ±1 mm (root-mean-square). Snapshots of the catheter are shown in FIG. 5.

EXAMPLE 5

In vivo Testing of Gd-Dtpa-Filled Catheter Visualization

Figure 6:
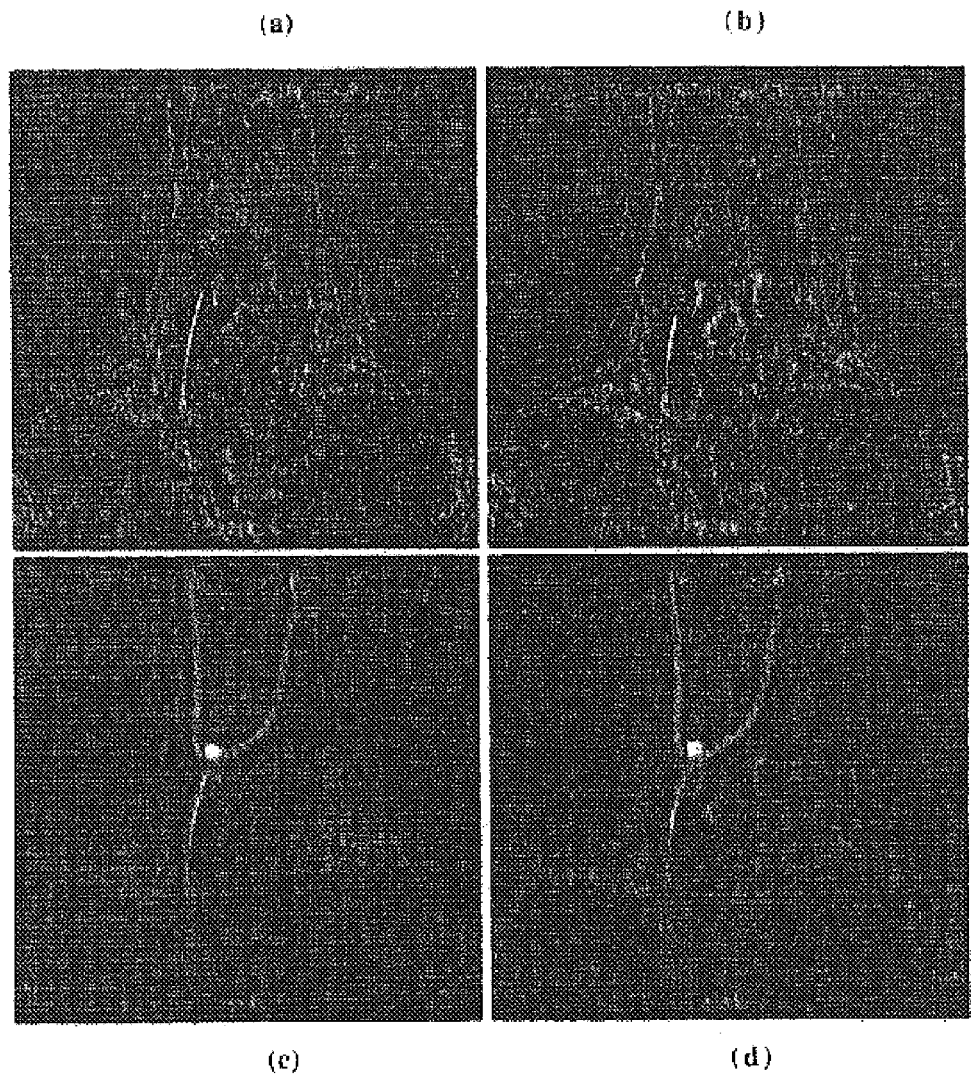
FIG. 6 is temporal MR snapshots of a Gd-DTPA-filled catheter moving in the common carotid of a canine.

For in vivo evaluation, commercially-available single lumen catheters filled with Gd-DTPA (4–6% solution), ranging in size between 3 and 6 French (1–2 mm), and catheter/guide-wire combinations were imaged either in the aorta or in the carotid artery of four canines. All animal experiments were conducted in conjunction with institution-approved protocols and were carried out with the animals under general anesthesia. The lumen of the catheter is open at one end and closed at the other end by a stopcock. This keeps the Gd-DTPA solution in the catheter. The possibility of Gd-DTPA leaking out of the catheter lumen through the open end was small and is considered safe because the Gd-DTPA used in these experiments is commercially available and approved for use in MR. Reconstructed images made during catheter tracking were superimposed on previously acquired angiographic "roadmap" images typically acquired using a 3D TRICKS imaging sequence (F. R. Korosec, R. Frayne, T. M. Grist, C. A. Mistretta, 36 *Magn. Reson. Medicine.* (1996) 345–351, incorporated herein by reference) in conjunction with either an intravenous or intra-arterial injection of Gd-DTPA (0.1 mmol/kg). On some occasions, subtraction techniques were used to eliminate the background signal from the catheter images prior to superimposing them onto a roadmap image. Snapshots of the canine carotids and aortas are shown in FIGS. 6 and 7, respectively.

EXAMPLE 6

In vivo Catheter MR Visualization

Using canines, a catheter coated with a coating in accordance with the present invention/guide-wire combination is initially positioned in the femoral artery. Under MR guidance, the catheter is moved first to the aorta, then to the carotid artery, then to the circle of Willis, and on to the middle cerebral artery. The catheter movement is clearly seen in the vessels. The length of time to perform this procedure and the smallest vessel successfully negotiated is recorded.

EXAMPLE 7

Paramagnetic Ion Safety Testing

A gadolinium leaching test is performed to ascertain the stability of the Gd-DTPA complex. Polyethylene sheets coated with a coating in accordance with the present invention are subjected to simulated blood plasma buffers and blood plasma itself. NMR scans are taken and distinguish between chelated $Gd^{3+}$ and free $Gd^{3+}$. The results indicate that the $Gd^{3+}$ complex is stable under simulated blood conditions.

EXAMPLE 8

Biocompatibility Testing

A biocompatibility test is carried out on polymeric surfaces coated in accordance with the present invention using an adsorption method of serum albumin labeled with fluorescent dyes. If the albumin is irreversibly adsorbed as detected by fluorescence of coated catheter surfaces, the coat is adjudged to be bioincompatible.

EXAMPLE 9

Determination of Coating Signal Intensities

A clinical 1.5 T scanner (Signa, General Electric Medical Systems) is used to determine the optimal range of coating densities (in mmol $Gd^{3+}$ $m^{-2}$) for producing appreciable signal enhancement on a series of silicon wafers coated with a polyethylene-Gd-containing coating in accordance with the present invention. The wafers are placed in a water bath and scanned cross-sectionally using a moderately high-resolution fast gradient-recalled echo (FGRE) sequence with TR≈7.5 ms/TE≈1.5 ms, 256×256 acquisition matrix and a 16 cm×16 cm field-of-view (FOV). The flip angle is varied from 10° to 90° in 10° increments for each coating density. A region of interest (ROI) is placed in the water adjacent to the wafer and the absolute signal is calculated.

For calibration of signal measurements obtained in different imaging experiments, a series of ten calibration vials is also imaged. The vials contain various concentrations of Gd-DTPA, ranging from 0 mmol $mL^{-1}$ to 0.5 mmol $mL^{-1}$. This range of concentrations corresponds to a range of T1 relaxation times (from <10 ms to 1000 ms) and a range of T2 relaxation times. The signals in each vial are also measured and used to normalize the signals obtained near the wafers. Normalization corrections for effects due to different prescan settings between acquisitions and variable image scaling are applied by the scanner. A range of concentrations in the vials facilitates piece-wise normalization. An optimal range of coating densities is determined.

In summary, the present invention provides a method of visualizing medical devices under MR guidance utilizing a coating, which is a polymeric-paramagnetic ion complex, on the medical devices.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that can lawfully be accorded the appended claims.

What is claimed is:

1. A method of making an existing medical device magnetic-resonance imageable, wherein the medical device has a surface, a portion of which is made from or coated with a solid polymer, the method comprising:

treating at least a portion of the solid-polymer surface of the medical device to yield at least one surface functional group thereon, the surface functional group being an amino group or a carboxyl group;

covalently linking a chelate to the surface functional group; and coordinating a paramagnetic-metal ion ($M^{n+}$) with the chelate to form a paramagnetic-metal-ion/chelate complex that is magnetic-resonance imageable, the paramagnetic-metal-ion/chelate complex being covalently linked to the medical device, wherein M is a paramagnetic ion and n is an integer that is 2 or greater.

2. The method of claim 1, wherein treating at least a portion of the solid-polymer surface comprises plasma treating at least a portion of the solid-polymer surface.

3. The method of claim 2, wherein plasma treating at least a portion of the solid-polymer surface comprises plasma treating the surface with a plasma gas which is urea, ammonia, a nitrogen-hydrogen combination or a combination thereof, and wherein the surface functional group is an amino group.

4. The method of claim 2, wherein plasma treating at least a portion of the solid-polymer surface comprises plasma treating the surface with a plasma gas which is carbon dioxide or oxygen, and wherein the surface functional group is a carboxyl group.

5. The method of claim 1, wherein the chelate is covalently linked to the surface functional group by an amide linkage.

6. The method of claim 1, wherein the polymer is selected from the group consisting of polyethylenes, polypropylenes, polyesters, polyamides, polyfluoroethylene and polyurethanes.

7. The method of claim 1, wherein M is a lanthanide or is a transition metal which is iron, manganese, chromium, cobalt or nickel.

8. A medical device capable of being magnetic-resonance imaged, the device comprising:

a solid-polymer surface having functional groups linked thereto, the functional groups being amino groups or carboxyl groups;

a chelate covalently linked to at least one of the functional groups on the solid-polymer surface; and a paramagnetic-metal ion coordinated with the chelate to form a paramagnetic-metal-ion/chelate complex capable of being magnetic-resonance imaged, the paramagnetic-metal-ion/chelate complex being covalently bonded to the medical device such that the complex is substantially non-absorbable by a living organism upon being inserted therein.

9. The device of claim 8, wherein the polymer is selected from the group consisting of polyethylenes, polypropylenes, polyesters, polyamides, polyfluoroethylene and polyurethanes.

10. The device of claim 8, wherein the paramagnetic metal is a lanthanide or is a transition metal which is iron, manganese, chromium, cobalt or nickel.

11. The device of claim 8, wherein the functional groups linked to the solid-polymer surface are formed by plasma treating the surface with a plasma gas or vapor.

12. The device of claim 11, wherein the plasma gas is urea, ammonia, a nitrogen-hydrogen combination or a combination thereof, and wherein the surface functional group is an amino group.

13. The device of claim 11, wherein the plasma gas is carbon dioxide or oxygen, and wherein the surface functional group is a carboxyl group.

14. The device of claim 8, wherein the chelate is covalently linked to the surface functional group by an amide linkage.

15. A magnetic-resonance-imaging system comprising:

a magnetic-resonance device for generating a magnetic-resonance image of a target object in an imaging region; and an instrument for use with the target object in the imaging region, the instrument including a body sized for use in the target object, the body being made at least partially from a solid-base polymer, the solid-base polymer being surface functionalized via plasma treatment to yield functional groups linked thereto, the functional groups being amino groups or carboxyl groups and having chelating agents covalently linked thereto, and the chelating agents having paramagnetic metal ions coordinated therewith to form paramagnetic-metal-ion/chelate complexes capable of being magnetic-resonance imaged.

16. The system of claim 15, wherein the polymer is selected from the group consisting of polyethylenes, polypropylenes, polyesters, polyamides, polyfluoroethylene and polyurethanes.

17. The system of claim 15, wherein the paramagnetic metal is a lanthanide or is a transition metal which is iron, manganese, chromium, cobalt or nickel.

18. The system of claim 15, wherein the functional groups linked to the solid-polymer surface are formed by plasma treating the surface with a plasma gas selected from the group consisting of urea, ammonia, a nitrogen-hydrogen combination, carbon dioxide and oxygen.

19. The system of claim 15, wherein at least one of the functional groups is an amino group.

20. The system of claim 15, wherein at least one of the functional groups is a carboxyl group.

* * * * *

UNITED STATES PATENT AND TRADEMARK OFFICE
CERTIFICATE OF CORRECTION

PATENT NO. : 6,896,873 B2
DATED : May 24, 2005
INVENTOR(S) : Richard Frayne et al.

It is certified that error appears in the above-identified patent and that said Letters Patent is hereby corrected as shown below:

Column 1,
Line 29, insert:
-- This invention was made with United States government support awarded by the following agencies:

COM   Grant No: 70NANB5H0054
    NIH    Grant No: HL57501; HL57983
    NSF    Grant Nos: EEC-8721545; DMR-9203289; DMR-9711226
    VA     Grant No: V607P-2283

The United States has certain rights in this invention. --.

Signed and Sealed this

Thirty-first Day of January, 2006

JON W. DUDAS
*Director of the United States Patent and Trademark Office*